United States Patent [19]

Santilli

[11] 4,266,050

[45] May 5, 1981

[54] 1,2-DIHYDRO-4-HYDROXY-2-IMINO-N-SUBSTITUTED-3-QUINOLINECARBOXAMIDE DERIVATIVES

[75] Inventor: Arthur A. Santilli, Havertown, Pa.

[73] Assignee: American Home Products Corporation, New York, N.Y.

[21] Appl. No.: 165,310

[22] Filed: Jul. 2, 1980

[51] Int. Cl.³ .................. C07D 215/14; C07D 215/06; C07D 413/12
[52] U.S. Cl. ..................................... 544/128; 546/156
[58] Field of Search .......................... 544/128; 546/156

[56] References Cited

U.S. PATENT DOCUMENTS

| | | | |
|---|---|---|---|
| 4,107,310 | 8/1978 | Allais et al. | 546/156 |
| 4,146,625 | 3/1979 | Lee | 546/156 |

OTHER PUBLICATIONS

Coppola et al., *J. Heterocyclic Chem.*, vol. 16, pp. 1605–1610 (1979).

*Primary Examiner*—John M. Ford
*Attorney, Agent, or Firm*—Richard K. Jackson

[57] ABSTRACT

1,2-Dihydro-4-hydroxy-2-imino-N-substituted-3-quinolinecarboxamide derivatives are disclosed as diuretic agents.

7 Claims, No Drawings

1,2-DIHYDRO-4-HYDROXY-2-IMINO-N-SUBSTITUTED-3-QUINOLINECARBOXAMIDE DERIVATIVES

BRIEF DESCRIPTION OF THE INVENTION

In accordance with this invention there is provided a group of 1,2-dihydro-4-hydroxy-2-imino-N-substituted-3-quinolinecarboxamide derivatives which act as diuretic agents useful in the treatment of conditions requiring diuresis therapy. Some of the compounds within the group of compounds of this invention, specifically those devoid of a heterocyclic alkylamide moiety possess in addition to diuretic activity, excellent gastric anti-secretory activity and those compounds are useful in the treatment of peptic ulcer disease. As anti-secretory agents, the compounds of this invention reduce (1) total gastric volume, (2) hydrogen ion secretion, or (3) hydrogen ion concentration. The reduction of any one of these parameters aids in relieving the debilitating effects of peptic ulcer disease is an established, beneficial procedure.

DETAILED DESCRIPTION OF THE INVENTION

The diuretic agents of this invention are compounds of the formula:

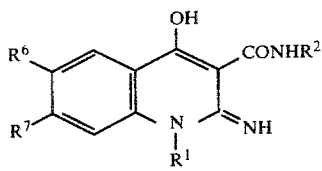

in which
$R^1$ is hydrogen or alkyl of one to six carbon atoms;
$R^2$ is hydrogen, alkyl of one to six carbon atoms, allyl, 2-hydroxyethyl, 2-alkoxyethyl in which the alkoxy group has from one to six carbon atoms or 2-(4-morpholinyl)ethyl;
$R^6$ is hydrogen, chlorine or bromine
and
$R^7$ is hydrogen or, when $R^6$ is hydrogen, chlorine or bromine;
or a pharmaceutically acceptable salt thereof.

The basic amides, such as the 2-(4-morpholinyl)ethyl amide, are capable of forming acid addition salts and may be employed in that form. Pharmaceutically acceptable acids from which salts may be formed include such acids as hydrochloric, hydrobromic, sulfuric, phosphoric, methane sulfonic, nitric, p-toluene sulfonic, acetic, citric, maleic, succinic acid and the like.

The compounds of this invention are prepared by reaction of chloro- or bromo-substituted-N-alkyl isatoic anhydride with sodium 2-cyano-N-substituted-acetamide as follows:

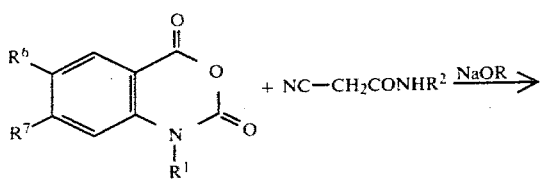

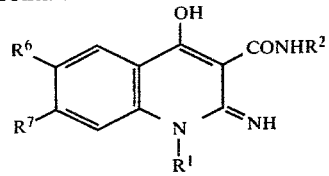

The gastric anti-secretory activity possessed by certain compounds of this invention was established by the following scientifically recognized, standard test for gastric anti-secretory activity:

Male Charles River rats of Sprague-Dawley strain and 190 to 240 grams body weight are food deprived for 24 hours with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was administered intraduodenally. The rats are sacrificed by $CO_2$ asphyxiation four hours after pyloric ligation. The stomachs are removed and the gastric contents emptied into graduated centrifuge tubes. The gastric samples are centrifuged for 20 minutes and those obviously contaminated by food, blood or feces are discarded. The volume of gastric fluid is recorded and the acid concentration of 1.0 milliliter sample aliquots is measured by electrometric titration to pH 7.0 with 0.1 N NaOH. The calculated product of gastric volume (ml/4 hr.) and acid concentration (mEq/L) estimates the total acid output (TAO, mEq/4 hr.) over the four-hour test period. An analysis of variance is performed on these data to determine statistically significant ($p<0.05$) deviation between control versus drug-treated groups.

The following Examples are presented to illustrate the preparation of the claimed compounds. The gastric anti-secretory activity of those compounds demonstrating that activity is expressed at the end of each Example as the percent inhibition of acid secretion in drug treated compared to control groups based upon i.d. administration of 32 mg/kg of the tested compound.

EXAMPLE 1

6-Chloro-1,2-dihydro-4-hydroxy-2-imino-1-methyl-N-[2-(4-morpholinyl)ethyl]-3-quinolinecarboxamide To a solution of 0.92 g. (0.04 g. atoms) of sodium dissolved in 50 ml. of absolute ethanol was added 7.88 g. (0.04 mole) of 2-cyano-N-(2-morpholinoethyl)acetamide. The solvent was removed in a rotary evaporator in vacuo. Dimethyl formamide (50 ml.) was added to the residue followed by 8.46 g. (0.04 mole) of 5-chloro-N-methylisatoic anhydride. The reaction mixture was heated under reflux for 4 hours, cooled in ice and then poured into 1-liter of water. The resulting precipitate was collected and recrystallized from ethanol giving 5.6 g. of product, m.p. 211°–213° C.

Analysis for: $C_{17}H_{21}ClN_4O_3$: Calculated: C, 55.97; H, 5.80; N, 15.36: Found: C, 55.69; H, 5.65; N, 15.41.

EXAMPLE 2

6-Chloro-1,2-dihydro-4-hydroxy-2-imino-N-(2-methoxyethyl)-1-methyl-3-quinolinecarboxamide To a solution containing 0.92 g. (0.04 g. atom) of sodium dissolved in 100 ml. of absolute ethanol was added 5.28 g. (0.04 mole) of 2-cyano-N-(2-methoxyethyl)acetamide. The solvent was removed in a rotary evaporator in vacuo and 100 ml. of dimethyl formamide was then added followed by 8.46 g. (0.04 mole) of 5-chloro-N-methylisatoic anhydride. The reaction mixture was heated under reflux for 3 hours with stirring, cooled in ice and then poured into 1-liter of ice water. The precipitate which formed was collected and recrystallized from EtOH giving 4.7 g. of product, m.p. 209°–211° C.

Analysis for: $C_{14}H_{16}ClN_3O_3$: Calculated: C, 54.29; H, 5.21; N, 13.56: Found: C, 54.21; H, 5.30; N, 13.72. 78% inhibition at 32 mg/kg i.d.

EXAMPLE 3

1,2-Dihydro-4-hydroxy-2-imino-N-(2-methoxyethyl)-1-methyl-3-quinolinecarboxamide To a solution containing 2.3 g. (0.1 g. atom) of sodium in 250 ml. of absolute ethanol was added 14.2 g. (0.1 mole) of 2-cyano-N-(2-methoxyethyl)acetamide. The solvent was removed in a rotary evaporator in vacuo and 200 ml. of dimethyl formamide was added followed by 18.6 g. (0.1 mole) of N-methylisatoic anhydride. The reaction mixture was heated under reflux for 2 hours, cooled in ice and then poured into 2-liters of water. The reaction mixture was allowed to stand in a cold room overnight. The resulting precipitate amounted to 11.9 g., m.p. 208°–210° C. Recrystallization from ethanol gave 7.3 g. of product, m.p. 214°–216° C.

Analysis for: $C_{14}H_{17}N_3O_3$: Calculated: C, 61.08; H, 6.22; N, 15.26: Found: C, 60.99; H, 6.14; N, 15.17. 89% inhibition at 32 mg/kg i.d.

EXAMPLE 4

6-Chloro-1,2-dihydro-4-hydroxy-2-imino-1-methyl-N-(2-propenyl)-3-quinolinecarboxamide To a solution containing (0.1 g. atom) of sodium dissolved in 250 ml. of absolute ethanol was added 12.4 g. (0.1 mole) of 2-cyano-N-(2-propenyl)acetamide. The ethanol was removed in a rotary evaporator, in vacuo, and then replaced with 200 ml. of dimethyl formamide. 5-Chloro-N-methyl-isatoic anhydride (21.2 g.; 0.1 mole) was added and the reaction mixture heated under reflux for 2 hours, cooled and then poured into 1-liter of water. The resulting precipitate was collected on a filter and recrystallized from ethanol giving 10.9 g. (m.p. 220°–222° C.) of product.

Analysis for: $C_{14}H_{14}ClN_3O_2$: Calculated: C, 57.64; H, 4.84; N, 14.40: Found: C, 57.49; H, 4.80; N, 14.41. 79% inhibition at 32 mg/kg i.d.

EXAMPLE 5

6-Chloro-1,2-dihydro-4-hydroxy-N-(2-hydroxyethyl)-2-imino-1-methyl-3-quinolinecarboxamide To a solution containing 2.3 g. (0.1 mole) of sodium dissolved in 250 ml. of absolute ethanol was added 12.8 g. (0.1 mole) of 2-cyano-N-(2-hydroxyethyl)acetamide. The solvent was removed in a rotary evaporator in vacuo and 200 ml. of dimethyl formamide was then added followed by 21.2 g. (0.1 mole) of 5-chloro-N-methylisatoic anhydride. The reaction mixture was heated under reflux for 2 hours, with stirring, cooled in ice and then poured into 1-liter of water. The resulting precipitate was collected on a filter placed in 200 ml. of boiling ethanol and filtered. The filter cake was recrystallized from DMF-$H_2O$, giving a product with m.p. 234°–237° C.

Analysis for: $C_{13}H_{14}ClN_3O_3$: Calculated: C, 52.80; H, 4.77; N, 14.21: Found: C, 52.63; H, 4.58; N, 14.09: 74% inhibition at 32 mg/kg i.d.

EXAMPLE 6

7-Chloro-1,2-dihydro-4-hydroxy-2-imino-1-methyl-N-(2-propenyl)-3-quinolinecarboxamide To a solution of 0.92 g. (0.04 g. atom) of sodium in 250 ml. of ethanol was added 4.96 g. (0.04 mole) of N-allyl-2-cyanoacetamide. The reaction mixture was stirred for a few minutes and the ethanol was removed in a rotary evaporator. The ethanol was then replaced with 200 ml. of dimethyl formamide. To this solution was added 8.46 g. (0.04 mole) of 4-chloro-N-methyl isatoic anhydride. The reaction mixture was heated under reflux for 2 hours. The reaction mixture was cooled in ice and poured into 1-liter of water. The reaction mixture was acidified with conc. hydrochloric acid. The precipitate was collected on a filter and amounted to 3.5 g., m.p. 212°–214° C. Recrystallization from ethanol gave 1.5 g. of product, m.p. 216°–218° C.

The diuretic activity of the compounds of this invention was established following the rat five hour oral diuretic assay of Lipschitz et al., J. Pharmacol. Exp. Therap. 79, 97 (1943) as follows. Male Sprague-Dawley rats 14 to 17 weeks old, 175–200 grams are used. At four P.M. on the day before an experiment, food and water are removed. The next morning the rats are given an oral physiological saline prime dose of 25 ml/kg. containing the compound being tested. The compound being tested is given to eight rats and saline alone is given to eight rats as a control. The animals are placed in metabolism cages, two rats per cage and their urine is collected for five hours. The volume of urine is then determined. The results of testing the compounds produced in Examples 1–6 are expressed in the following Table:

TABLE

| Compound | Oral Dose mg/kg | ml. Excret. | Control Saline (ml) Excret. |
| --- | --- | --- | --- |
| Example 1 | 25 | 34.75 | 24.5 |
| Example 2 | 25 | 66.5 | 27.25 |
|  | 5.0 | 42.0 | 38.75 |
| Example 3 | 25 | 49.75 | 35.0 |
|  | 5.0 | 42.0 | 26.0 |
| Example 4 | 25 | 71.5 | 29.5 |
|  | 2.5 | 55.0 | 35.5 |
|  | 5.0 | 69.5 | 35.5 |
|  | 10.0 | 68.0 | 35.5 |
|  | 25.0 | 62.5 | 35.5 |
| Example 5 | 25 | 63.25 | 38.25 |
| Example 6 | 25 | 67.5 | 25.5 |
|  | 25 | 75.5 | 38.5 |
|  | 5 | 62.5 | 38.5 |

The dosage regimen for therapeutic use of the diuretic agents disclosed herein will vary with the mode of administration, size and age of the person under treatment as well as the severity of the dysfunction. Therefore, treatment of the condition requiring diuresis must be individualized for the patient under the guidance of the attending physician. The use of the anti-secretory agents disclosed herein must similarly be controlled by the physician. Where two conditions occur simultaneously in the same patient, requiring treatment of peptic ulcer disease as well as diuresis, the 4-hydroxy-2-imino-3-quinolinecarboxamides afford the decided advantage of single compound treatment for both problems. Where the conditions occur separately, the second activity of the claimed compounds is not deleterious and not contraindicative of applicability of the treatment.

The compounds of this invention may be administered by conventional oral or parenteral routes as solids, liquids or isotonic solutions. Conventional adjuvants known to the art may be combined with the compounds disclosed herein to provide compositions and solutions for administration purposes although it is considered desirable and feasible to use the compounds neat or pure without additives other than for the purpose of providing suitable pharmaceutically acceptable solid or liquid dosage units.

What is claimed is:

1. A compound of the formula:

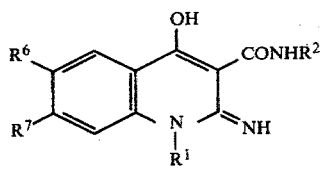

in which $R^1$ is hydrogen or alkyl of one to six carbon atoms;

$R^2$ is hydrogen, alkyl of one to six carbon atoms, allyl, 2-hydroxyethyl, 2-alkoxyethyl in which the alkoxy group has from one to six carbon atoms or 2-(4-morpholinyl)ethyl;

$R^6$ is hydrogen, chlorine or bromine and $R^7$ is hydrogen or, when $R^6$ is hydrogen, chlorine or bromine;

or a pharmaceutically acceptable salt thereof.

2. A compound of claim 1 which is 6-chloro-1,2-dihydro-4-hydroxy-2-imino-1-methyl-N-[2-(4-morpholinyl)ethyl]-3-quinolinecarboxamide or a pharmaceutically acceptable salt thereof.

3. A compound of claim 1 which is 6-chloro-1,2-dihydro-4-hydroxy-2-imino-N-(2-methoxyethyl)-1-methyl-3-quinolinecarboxamide.

4. A compound of claim 1 which is 1,2-dihydro-4-hydroxy-2-imino-N-(2-methoxyethyl)-1-methyl-3-quinolinecarboxamide.

5. A compound of claim 1 which is 6-chloro-1,2-dihydro-4-hydroxy-2-imino-1-methyl-N-(2-propenyl)-3-quinolinecarboxamide.

6. A compound of claim 1 which is 6-chloro-1,2-dihydro-4-hydroxy-N-(2-hydroxyethyl)-2-imino-1-methyl-3-quinolinecarboxamide.

7. A compound of claim 1 which is 7-chloro-1,2-dihydro-4-hydroxy-2-imino-1-methyl-N-(2-propenyl)-3-quinolinecarboxamide.

* * * * *